United States Patent [19]

Dunlap et al.

[11] 4,259,526

[45] Mar. 31, 1981

[54] PROCESS FOR THE PREPARATION OF MIXTURES OF POLYAMINES OF THE POLYAMINO-POLYARYL-POLYMETHYLENE TYPE

[75] Inventors: Kenneth L. Dunlap, New Martinsville, W. Va.; Hartmut Knofel, Odenthal, Fed. Rep. of Germany

[73] Assignees: Bayer Aktiengesellschaft, Leverkusen, Fed. Rep. of Germany; Mobay Chemical Corporation, Pittsburgh, Pa.

[21] Appl. No.: 13,765

[22] Filed: Feb. 21, 1979

[51] Int. Cl.³ .......................................... C07C 85/145
[52] U.S. Cl. .................................. 564/331; 564/333; 564/335
[58] Field of Search .................................. 260/570 D

[56] References Cited

U.S. PATENT DOCUMENTS

| 3,676,497 | 7/1972 | Recchia et al. ............... 260/570 |
| 3,857,890 | 12/1974 | Recchia et al. ............... 260/570 |
| 3,952,042 | 4/1976 | Knofel ...................... 260/570 X |
| 3,996,283 | 12/1976 | Knofel ........................ 260/570 |
| 4,061,678 | 12/1977 | Knofel et al. ................. 260/570 |
| 4,087,459 | 5/1978 | Knofel et al. ................. 260/570 |
| 4,093,658 | 6/1978 | Knofel et al. ................. 260/570 |
| 4,094,907 | 6/1978 | Knofel et al. ................. 260/570 |

*Primary Examiner*—Robert V. Hines
*Attorney, Agent, or Firm*—Gene Harsh; Joseph C. Gil

[57] ABSTRACT

The instant invention is directed to a process for the preparation of mixtures of polyamines of the polyamino-polyaryl-polymethylene type whereby the proportion or the ortno-substituted products are substantially increased. This increase is brought about by adding the acid catalyst to the aromatic amine/formaldehyde reaction mixture in two or more stages.

9 Claims, 1 Drawing Figure

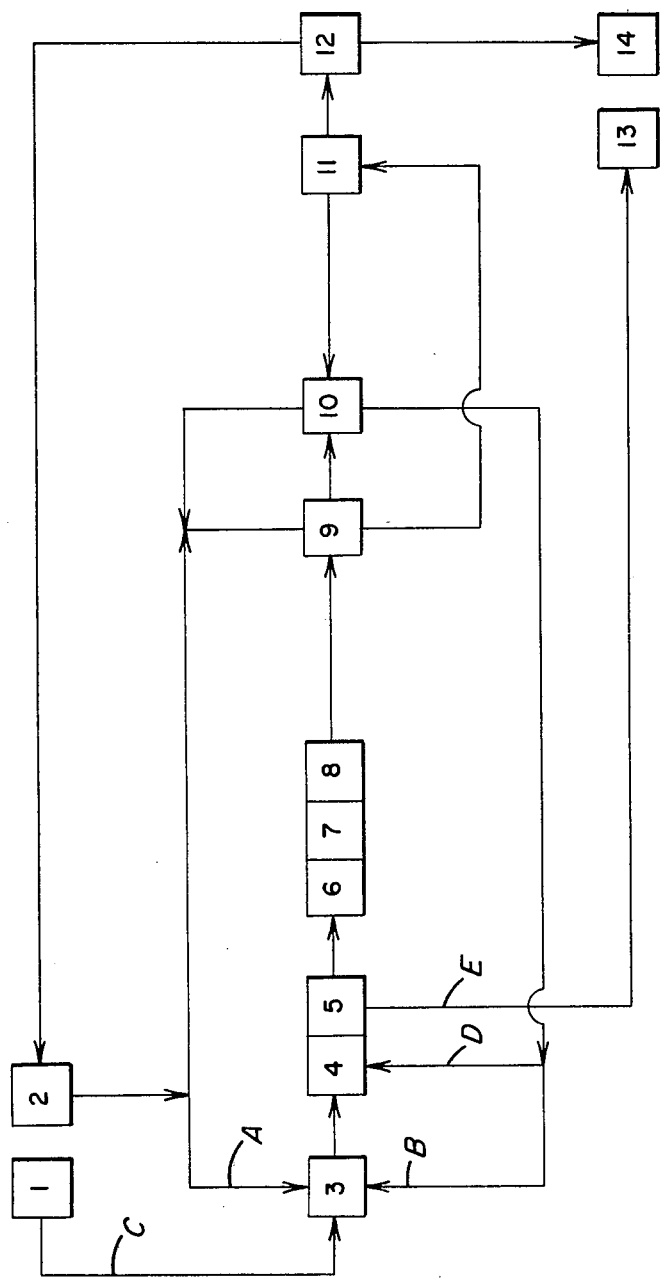

PROCESS FOR THE PREPARATION OF MIXTURES OF POLYAMINES OF THE POLYAMINO-POLYARYL-POLYMETHYLENE TYPE

BACKGROUND OF THE INVENTION

The preparation of di(aminoaryl) methanes and mixtures of methylene-bridged polyaryl polyamines containing the di(aminoaryl) methanes, by the acid condensation of aromatic amines and formaldehyde is well-known in the art (see e.g., U.S. Pat. No. 2,683,730). The di(aminoaryl) methanes and the polyamine mixtures are useful as intermediates in the preparation of the corresponding di- and polyisocyanates.

The di(aminoaryl) methanes prepared by procedures commonly used in the art generally consist mainly (i.e., 90 percent by weight or more) of the 4,4'-isomer with relatively minor amounts (i.e., less than 10 percent by weight) of the corresponding 2,4'-isomer. Recently, interest has been shown in di(aminoaryl) methanes containing higher amounts of the 2,4'-isomer. Various procedures have been suggested for the production of such high 2,4'-isomer content materials. Illustrative are the techniques described in U.S. Pat. No. 3,362,979 (process using acidic siliceous catalyst); 3,277,173 (process conducted in the presence of controlled amounts of water); 3,857,890 (removal of acid after aminobenzylamine formation); and 4,071,558 (process using specified catalyst); and Belgian Pat. No. 648,787 (process using controlled temperatures).

It has now been found that di(aminoaryl) methanes and methylene bridged polyaryl polyamines with substantially increased ortho-substitution can be produced using the novel procedure described herein.

BRIEF DESCRIPTION OF THE DRAWING

The FIGURE represents a flow diagram of one embodiment of the instant invention and is more fully described in Example 6.

DESCRIPTION OF THE INVENTION

The instant invention is directed to a process for the production of mixtures of polyamines of the polyaminopolyaryl-polymethylene type comprising:

(a) reacting an aromatic amine with formaldehyde in the presence of an aqueous acid catalyst at a temperature of from 10° to 100° C. or subjecting a condensate which has been obtained from an aromatic amine and formaldehyde in the absence of any acid catalyst to a first rearrangement in the presence of an aqueous acid catalyst at a temperature of from 10° to 100° C. to obtain a secondary amine-containing intermediate mixture, the amount of acid employed corresponding to a protonation degree of from 0.1 to 25%, (b) adding aqueous acid catalyst to the mixture of step (a), the amount of acid added being such that the total amount of acid in the mixture corresponds to a protonation degree of from 10 to 100%, (c) subjecting the resultant mixture of step (b) to a rearrangement reaction at a temperature of from 75° C. to 150° C. to obtain a condensation mixture containing said mixture of polyamines, and (d) recovering said polyamines.

The term "protonation degree" as used herein is defined as the percentage of all amine nitrogen atoms which have been protonated, i.e. which are in the form of amine or ammonium salts.

It is generally known in the art that the acid condensation of aromatic amines and formaldehyde occurs in two distinct stages. For purposes of illustration, in the case of aniline and formaldehyde, the reaction sequence occurs as follows:

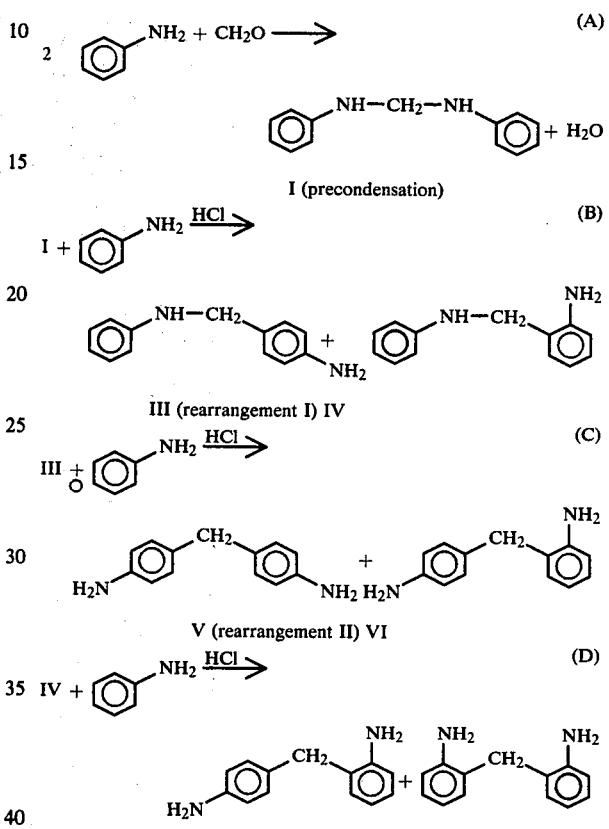

As is known, the rearrangement of N-(p-aminobenzyl) aniline III, leads only to the formation of the 2,4'-and the 4,4'-isomers (i.e. sequence (C)), while the rearrangement of N-(o-aminobenzyl) aniline, IV, leads only to the formation of the 2,2'-and 2,4'-isomers.

As is well recognized in the art, the formation of the N-(aminobenzyl) amines III and IV is accompanied by formation of the corresponding oligomeric products. The mixture of isomers of the type III and IV and the oligomeric forms thereof is hereinafter referred to as the "secondary amine-containing intermediate mixtures".

In the final rearrangement reaction set forth above, the intermediates III and IV rearrange to form the corresponding di(aminophenyl) methanes. The 2,2'-isomer is also formed but in a relatively minor amount with highly catalyzed conventional processes. As is also recognized, the final rearrangement also yields the corresponding polyamines.

Of the stages noted above, the first two, i.e., the precondensation (which occurs even in the absence of acid catalyst and which therefore can also be carried out in a first independent step i.e. at 10° to 100° C. in the absence of any catalyst) and the first rearrangement, generally occur when the aniline and formaldehyde are brought together in the presence of the acid catalyst at temperatures of from 10° to 100° C. The reaction is exothermic and, unless controlled by cooling, the temperature will rise substantially. The final stage of the process, i.e., the rearrangement of the intermediates, does not take place to a significant degree until the reaction mixture is heated, generally to a temperature in excess of 60° C. Essentially, the intent of the instant invention was to increase the amount of intermediate of type IV produced to thereby increase the amount of ortho-substitution in the final product. It has now been found that the yield of ortho-substitution is unexpectedly increased when the acid catalyst is added in two or more stages. The first addition occurs at the beginning of the reaction this means that the first portion of the catalyst is added either to the condensate which has been obtained from the aromatic amine and formaldehyde in the absence of catalysts or to the reaction mixture containing aromatic amine and formaldehyde while the subsequent addition or additions occur after formation of the intermediate mixture but before the completion of the final rearrangement.

In carrying out the instant invention, the formation of the secondary amine-containing intermediate mixture is carried out in a conventional manner except for the amount of acid initially present as discussed below. Generally, the aromatic amine and formaldehyde are either brought together under aqueous conditions in the presence of the specified amount of catalyst or the specified amount of catalyst is added to the condensate formed from the aromatic amine and formaldehyde in the absence of any catalyst. The order which the reactants are brought together is not critical although it is found advantageous to add the formaldehyde to a preformed mixture of aromatic amine and acid. The condensation reaction between the aromatic amine and formaldehyde is exothermic and, if desired, the reaction mixture can be cooled in order to keep the reaction temperature from rising beyond any desired level. The reaction temperature can also be controlled by the rate at which the reactants are brought together. Advantageously the reaction according to step (a) is allowed to take place at a temperature within the range of about 10° C. to 100° C. Preferably the reaction temperature is maintained within the range of from about 40° C. to about 100° C. The reaction temperature can be maintained at a specific temperature within this range or can be allowed to rise or fall at will, by adjusting rates of addition of reactants or like means, provided the reaction temperature does not pass outside the above limits. It is found that the higher temperatures in the above range can be tolerated more readily as the amount of acid initially present in the reaction mixture is reduced.

The proportions in which the aromatic amine, formaldehyde, and initial acid catalyst are brought together are determinative of the overall yield of diamine and, to a certain extent, of the proportion of ortho- and para-substitution in the final product. Advantageously, the molar ratio of aromatic amine to formaldehyde is from 2:1 to 15:1 and preferably from 3:1 to 10:1. While the lower limit of concentration of aromatic amine to formaldehyde is critical in terms of the overall result achieved in the process, the upper limit of proportions is free from such criticality and is dictated largely by economic considerations.

The amount of acid catalyst employed in the first stage of the process of the invention can vary over wide limits and advantageously corresponds to a protonation degree of from 0.1 to 25%. Preferably the amount of acid employed initially corresponds to a protonation degree of from 0.2 to 10% and most preferably corresponds to a protonation degree of from 0.3 to 7%.

Any of the acid catalysts hitherto employed in the art, including those specifically disclosed in the prior art cited above, can be used as catalyst in the process of this invention. Suitable catalysts include water-soluble acids having pKa values below 2.5 and preferably below 1.5. Specific examples include hydrochloric acid, hydrobromic acid, sulphuric acid, trifluoroacetic acid, methane sulphonic acid, trifluoromethane sulphonic acid, benzene sulphonic acid, or phosphoric acid. Hydrochloric acid is the preferred catalyst. The above-mentioned acids can also be used in admixture with acid or neutral salts of such acids, e.g. the corresponding ammonium salts or the corresponding alkali metal salts. If desired, the ammonium salts formed from the aforesaid acids and from the aromatic amine used as starting material or resulting as condensation products in any stage of the process can be used as the only catalysts.

The progress of the condensation of the aromatic amine and formaldehyde in the above first stage reaction step (a) can be followed readily by conventional analytical techniques such as infrared spectroscopy, NMR spectroscopy and the like; formation of the secondary amine-containing intermediate mixture is detected and followed by any such techniques. In general, the additional quantity of acid catalyst can be added at any time after the intermediates are detected. Thus, the additional acid, which in all cases must be added, can be added at any time after the intermediate mixture is detected and prior to the completion of the final rearrangement step of condensation. The amount of additional acid catalyst added is such that the total amount of acid in the mixture (including the acid initially added) corresponds to a protonation degree of from 10 to 100% and preferably corresponds to a protonation degree of from 20 to 50%.

The time for which the mixture is heated in the final step is a function of the reaction conditions, particularly reaction temperature, employed in any given case. In general, the temperature for the final step will be from 75° to 150° C. The progress of the reaction can be followed by routine analytical procedures such as infrared spectroscopy, gas liquid phase chromatography and the like. When the reaction is adjudged to be complete by any of these analytical procedures, the reaction mixture is treated in any appropriate manner depending upon the ultimate intended use of the mixture of polyamines obtained. For example, the reaction mixture can be neutralized and distilled to remove excess aromatic amine and the mixture of polyamines so obtained is recovered as such. Alternatively, the latter mixture can be further distilled or subjected to separation by other means such as chromatography, fractional crystallization and the like, to recover in part, or in whole, the mixed or unmixed di(aminoaryl) methanes present in the reaction mixture.

One of the most favorable methods of recovering the final products from the reaction mixture is to extract them from the aqueous solution by means of a mixture of a hydrophobic solvent and the starting aromatic amine as disclosed in U.S. Pat. No. 3,996,283, the disclosure of which is herein incorporated by reference. In using the extraction process according to the present invention, the aqueous phase is recycled to the first and second stages in the amounts corresponding to the protonation degrees specified above. In general, if high aniline/formaldehyde ratios and/or high protonation degrees in step (b) are used, it is preferred to use the extraction process for product recovery. Conversely, with low aniline content and low protonation degrees, it is preferred to use the neutralization technique for product recovery.

The mixture of polyamines obtained directly from the above reaction, or the mixture of polyamines remaining after partial or complete removal of the di(aminoaryl)methane content thereof can be employed for any of the purposes for which such mixtures are employed in the art. For example, the mixture of polyamines can be employed as intermediates in the preparation, by phosgenation, of the corresponding polymethylene polyaryl polyisocyanates. The latter are commonly employed in the preparation of polyurethane foams.

The di(aminoaryl)methanes, which can be isolated as described above, can also be used for any of the purposes for which such mixtures are conventionally employed in the art. For example, they can be used as curing agents for epoxy resins or as intermediates in the preparation, by phosgenation, of the corresponding di(isocyanatoaryl)methanes.

The process according to the invention can be carried out with any aromatic amines such as, for example, aniline; o-, m-, or p-chloroaniline; o-, m-, or p-bromoaniline; o-, m-, or p-anisidine; o-, m-, or p-phenetidine; o-, m-, or p-toluidine; o-, m-, or p-ethylaniline; o-, m-, or p-isopropylaniline; o-, m-, or p-xylidines; a- or β-naphthylamine; o-, m-, or p-benzylaniline; o-, m-, or p-cyclohexylaniline; 2,6-dimethylaniline; 2,6-diethylaniline; 2,6-diisopropylaniline, 2,4- or 2,6-diaminotoluene; o-, m-, or p-diaminobenzene; N-methyl-, N-ethyl-, N-propyl-, N-butyl-, N-hydroxyethyl- or N-chloroethylaniline; o-, m-, or p-methyl-N-methylaniline; o-, m-, or p-methyl-N-ethylaniline; o-, m-, or p-chloro-N-methylaniline; o-, m-, or p-chloro-N-ethylaniline; o-, m-, or p-thioanisidine; or any mixtures of the aforementioned amines, or mixtures of the aforementioned amines with their formaldehyde condensation products of the diaryl methane type. Aniline is preferably used as the starting amine in the process according to the invention.

The formaldehyde used in the process according to the invention can be employed in the form of an aqueous or aqueous-methanolic solution, or even in the form of a formaldehyde-donor, for example, methylal, trioxane or paraformaldehyde. An aqueous formaldehyde solution is preferably used in the process according to the invention.

As previously mentioned the mixtures obtained in accordance with the process of the invention, whether in the form of the isolated diamine or of the mixture of methylene-bridged polyaryl polyamines, contain a substantial proportion, of ortho-substitution. The mixtures of the invention generally contain from 70 to 95 percent by weight of the diamine with the balance being higher amines. In the case of aniline/formaldehyde products, the mixtures generally contain no more than 5% by weight (based on diamine present) of the 2,2'-isomer, with the 2,4'-isomer content being as high as 40% by weight.

The process of the invention can be carried out in a batch-type process or can be carried out either partly or wholly in a continuous manner. For example, the first step in the reaction process (i.e. the condensation of aromatic amine and formaldehyde) can be carried out in a single batch or in a continuous process in which the reactants are fed continuously in the appropriate proportions to one end of a reaction zone and the mixture of aminoarylamines withdrawn continuously from the other end thereof. The additional acid catalyst can be added to the resulting mixture in a batch procedure or on a continuous basis. The mixture can then be passed continuously through a reaction zone maintained at a temperature within the range required to accomplish the final stage of the process. The desired final product is continuously withdrawn from the other end of the reaction zone. The rate of passage is adjusted so that the residence time of the mixture is appropriate to achieve conversion of the aminoarylamines to the desired mixture of methylenebridged polyaryl polyamines.

The following examples describe the manner and process of making and using the invention and set forth the best mode contemplated by the inventors of carrying out the invention but are not to be construed as limiting.

EXAMPLES

Example 1 (comparison example)

100 grams of 30% aqueous formaldehyde were added at 40° C. to an agitated mixture of 372 grams of freshly distilled aniline and 162 grams of 30% hydrochloric acid (0.3375 mol acid per mol aniline; protonation degree of 33.75%). The mixture was maintained at 40° C. for one hour. Then it was brought to reflux and kept under reflux for 3 hours. The mixture was neutralized with excess sodium hydroxide, separated from the aqueous brine solution, and freed of residual water and excess aniline. The resulting polyamine was composed of 81.9% diaminodiphenylmethane and 18.1% higher oligomers. The composition of the diaminodiphenylmethane was as follows: 0.3% 2,2'-isomer, 9.3% 2,4'-isomer, and 90.3% 4,4'-isomer.

Example 2

100 grams of 30% aqueous formaldehyde were added at 40° C. to a stirred mixture of 372 grams of aniline and 8 grams of 30% hydrochloric acid (0.017 mol acid per mol aniline; protonation degree of 1.7%). The temperature was maintained at 40° C. for one hour and then increased to 100° C. for one hour. 154 grams of 30% hydrochloric acid were then added to the mixture (0.35 mol acid total per mol aniline; protonation degree of 35%) and the reaction mixture was refluxed for an additional 3 hours. The mixture was neutralized, separated from the aqueous brine, and freed of residual water and excess aniline. The resulting polyamine contained 77.2% diaminodiphenylmethane and 22.8% higher oligomers. The diamine was comprised of 0.9% 2,2'-isomer 16.2% 2,4'-isomer, and 82.9% 4,4'-isomer.

Example 3

100 grams of an aqueous 30% solution of formaldehyde were added to a stirred mixture of 558 grams of aniline and 3.7 grams of 30% hydrochloric acid (0.005 mol acid per mol aniline; protonation degree of 0.5%) at 100° C. This mixture was refluxed for 30 minutes. 158.5 grams of 30% hydrochloric acid were then added to the mixture (0.23 mol acid total per mol aniline; protonation degree of 23%), and the reaction mixture was refluxed for an additional three hours. After neutralization and normal work-up (as described in the previous examples), the polyamine was found to contain 84.4% diaminodiphenylmethane and 15.6% higher oligomers. The diamine was composed of 2.5% 2,2'-isomer, 25.1% 2,4'-isomer, and 71.3% 4,4'-isomer.

Example 4

50 grams of aqueous 30% solution of formaldehyde were added to a stirred mixture of 465 grams of aniline and 10.1 grams of 30% hydrochloric acid (0.017 mol acid per mol aniline; protonation degree of 1.7%) at 100° C. The mixture was refluxed for 60 minutes, and then 125.1 grams of 30% hydrochloric acid were added (0.22 mol acid total per mol aniline; protonation degree of 22%). This reaction mixture was refluxed for an additional 2.5 hours, followed by neutralization with sodium hydroxide and normal work-up (as described in Example 1). The polyamine was composed of 89.0% diaminodiphenylmethane and 11.0% higher oligomers, and the isomer distribution of the diamine was 3.2% 2,2'-isomer, 30.6% 2,4'-isomer, and 66.0% 4,4'-isomer.

Example 5

100 grams of an aqueous 30% solution of formaldehyde were added to a stirred mixture of 558 grams of aniline and 12 grams of 30% hydrochloric acid (0.017 mol acid per mol aniline; protonation degree of 1.7%) at 80° C. This reaction mixture was held at 80° C. for one hour, and then the temperature was increased to 100° C. and maintained for one hour. 150 grams of 30% HCl were added to the mixture (0.23 mol acid total per mol aniline; protonation degree of 23%), and the mixture was refluxed for an additional three hours. After neutralization and normal work-up (described in Example 1) the composition of the product was found to be 83.8% diaminodiphenylmethane and 16.2% higher oligomers. The diamine was composed of 2.5% 2,2'-isomer, 25.4% 2,4'-isomer, and 72.1% 4,4'-isomer.

Example 6

This example relates to the extraction recovery process and will be described with reference to the figure.

Using a continuously operating laboratory testing equipment, in the first vessel of a reactor consisting of 6 vessels with stirrer (3-8), the streams (A) [aniline of storage container (2)] and (B) [recycled aqueous aniline- or polyarylamine hydrochloride solution of extractor (10)] are continuously mixed with one another and are reacted at 80° C. with aqueous formaline solution [stream (C) from container (1)]. The streams have the following composition (in g/h):

| Stream (A) | 2,050 | aniline |
|---|---|---|
| (B) | 171 | aniline |
| | 16 | polyarylamine |
| | 70 | hydrogen chloride |
| | 315 | water |
| (C) | 120 | formaldehyde |
| | 280 | water |

After an average residence time of about 25 minutes, a further amount of the aqueous arylamino hydrochloride solution, which is recycled from extractor (10) is added [stream (D)] to the second vessel (4) at 95° C.

| Stream (D) | 1,370 | aniline |
|---|---|---|
| | 128 | polyarylamine |
| | 560 | hydrogen chloride |
| | 2,524 | water |

After an average residence time of 10 minutes in (4), about 350 g/h water are distilled off [stream (E)] in a further vessel with stirrer (5) under normal pressure. Subsequently, the reaction is completed within one hour in vessels (6)–(8) under pressure, at 120°–130° C.

The completely reacted solution which has been cooled to 95° C., is subsequently put into an extraction system consisting of a first and second extraction column. In the first extraction column (9) at about 95° C., the reaction product is extracted from the aqueous phase using the organic phase from the second extraction column (10). [The aniline-xylene weight ratio is adjusted to 1.2:1.0 with aniline from container (2)]. About 6,500 g/h ortho-xylene is used as extraction agent for the second extraction column (10), which is recovered again in the distillation stage (11).

The aqueous arylaminohydrochloride solution yielded in (10) is divided into the streams (B) and (D) and is recycled.

The organic phase exiting from the extraction system is separated in the subsequent two-stage distillation system into ortho-xylene [first distillation stage (11)], aniline [second distillation stage (12)] and polyarylamine [distillation residue of (12)]. The recovered aniline together with the refined aniline supplied to the system is added to the reaction via the container (2).

The product yielded in the described example of this version of the inventive process (about 750 g/h) is collected is container (14) and has the following average composition:
  88 weight-% diaminodiphenylmethane
  12 weight-% high-ring polyamines with the following average composition of the diamino fraction:
    1.4 weight-% 2,2'-diaminodiphenylmethane
    18.5 weight-% 2,4'-diaminodiphenylmethane
    80.1 weight-% 4,4'-diaminodiphenylmethane.

Although the invention has been described in detail for the purpose of illustration, it is to be understood that such detail is solely for that purpose and that variations can be made wherein by those skilled in the art without departing from the spirit and scope of the invention except as it may be limited by the claims.

What is claimed is:

1. A process for the production of mixtures of polyamines of the polyamino-polyaryl-polymethylene type comprising:
   (a) reacting an aromatic amine with formaldehyde in the presence of an aqueous acid catalyst at a temperature of from 10° to 100° C. or subjecting a condensate which has been obtained from an aromatic amine and formaldehyde in the absence of any acid catalyst to a first rearrangement in the presence of an aqueous acid catalyst at a temperature of from 10° to 100° C. to obtain a secondary amine-containing intermediate mixture, the amount of acid employed corresponding to a protonation degree of from 0.1 to 25%,
   (b) adding aqueous acid catalyst to the mixture of step (a) in an amount such that the total amount of acid corresponds to a protonation degree of from 10 to 100%,
   (c) subjecting the resultant mixture of step (b) to a rearrangement reaction at a temperature of from 75° to 150° C. to obtain an acidic condensation mixture containing said polyamines, and
   (d) recovering said polyamines.

2. The process of claim 1, wherein said aromatic amine is aniline.

3. The process of claim 1, wherein the amount of acid employed in step (a) corresponds to a protonation degree of from 0.2 to 10%.

4. The process of claim 3, wherein the amount of acid employed in step (a) corresponds to a protonation degree of from 0.3 to 7%.

5. The process of claim 3, wherein the total amount of acid in step (b) corresponds to a protonation degree of from 20 to 50%.

6. The process of claim 1, wherein the molar ratio of aromatic amine to formaldehyde is from 2:1 to 15:1.

7. The process of claim 6, wherein the molar ratio of aromatic amine to formaldehyde is from 3:1 to 10:1.

8. A process for producing a mixture of polyamines of the polyamino-polyaryl-polymethylene type having an increased amount of ortho-substitution comprising
   (a) reacting an aromatic amine with formaldehyde in the presence of an aqueous acid catalyst at a temperature of from 10° to 100° C. or subjecting a condensate which has been obtained from an aromatic amine and formaldehyde in the absence of any acid catalyst to a first rearrangement in the presence of an aqueous acid catalyst at a temperature of from 10° to 100° C. to obtain a secondary amine-containing intermediate mixture, the amount of acid employed corresponding to a protonation degree of from 0.1 to 25%,
   (b) adding aqueous acid catalyst to the mixture of step (a) in an amount such that the total amount of acid corresponds to a protonation degree of from 10 to 100%,
   (c) subjecting the resultant mixture of step (b) to a rearrangement reaction at a temperature of from 75° to 150° C. to obtain an acidic condensation mixture containing said polyamines,
   (d) recovering said polyamines.

9. The process of claim 8, wherein said aromatic amine is aniline and said acid catalyst is hydrochloric acid.

* * * * *